United States Patent
Reinhardt et al.

(10) Patent No.: US 7,028,913 B2
(45) Date of Patent: Apr. 18, 2006

(54) PROCESS FOR HUMIDIFYING THE USEFUL SPACE IN AN INCUBATOR AND IN A CONTROLLED ATMOSPHERE INCUBATOR

(75) Inventors: Heiko Reinhardt, Hanau (DE); Waldemar Pieczarek, Bruchköbel (DE); Hermann Stahl, Mühlheim (DE)

(73) Assignee: Kendro Laboratory Products, GmbH, Hanau (DE)

( * ) Notice: Subject to any disclaimer, the term of this patent is extended or adjusted under 35 U.S.C. 154(b) by 595 days.

(21) Appl. No.: 10/068,947

(22) Filed: Feb. 11, 2002

(65) Prior Publication Data

US 2002/0110489 A1    Aug. 15, 2002

(30) Foreign Application Priority Data

Feb. 9, 2001    (DE) ............................... 101 06 349

(51) Int. Cl.
- *B01F 3/02* (2006.01)
- *G05D 21/00* (2006.01)
- *G05D 23/00* (2006.01)
- *A01K 31/20* (2006.01)
- *A01K 41/02* (2006.01)

(52) U.S. Cl. ..................... 236/44 C; 237/2 R; 237/3; 237/4; 236/44 R; 236/44 A; 236/44 B; 236/44 E; 236/46 R; 236/46 F; 422/99; 422/104

(58) Field of Classification Search ............... 237/2 R, 237/3, 4; 422/99, 104; 236/44 R, 44 A, 236/44 B, 44 C, 44 E, 46 R, 46 F
See application file for complete search history.

(56) References Cited

U.S. PATENT DOCUMENTS

| | | | | |
|---|---|---|---|---|
| 3,854,452 A | * | 12/1974 | Bardet | 119/319 |
| 4,572,427 A | * | 2/1986 | Selfridge et al. | 236/3 |
| 4,701,415 A | * | 10/1987 | Dutton et al. | 435/286.6 |
| 4,923,816 A | * | 5/1990 | Heeg et al. | 435/303.2 |
| 5,025,619 A | * | 6/1991 | Cannon | 119/300 |

(Continued)

FOREIGN PATENT DOCUMENTS

DE    3815528 C1 *    8/1989

*Primary Examiner*—Brian J. Sines
(74) *Attorney, Agent, or Firm*—Baker & Hostetler LLP

(57) ABSTRACT

For humidifying a work space in a gas-fed incubator, water in a heatable pan in the floor area of an inner container surrounding the work space is evaporated with temperature-controlled heating of the interior until a predetermined temperature is reached, whereby a dynamic equilibrium state between condensation and evaporation in the inner container is achieved as long as there are no disturbances. If a door for access to the inner container is opened, the open time until it is closed is detected and a period, during which the pan containing water is heated, is determined depending on the open time of the inner container. Here, the period features only a heating phase with a running time if the open time is within a predetermined time interval. The period further includes a secondary heating phase with a second running time if the open time exceeds the time interval. A gas-fed incubator operating according to the method has a work space in the inner container that can be closed by means of a door with temperature control of the interior, wherein in a floor area of the inner container there is a humidifier with at least one controllable heating element for an atmosphere of the inner container in the form of a pan holding a water bath. The door for closing the inner container has a door switch that is electrically connected to an input of a control unit for operation of the humidifier.

30 Claims, 4 Drawing Sheets

U.S. PATENT DOCUMENTS

| | | | |
|---|---|---|---|
| 5,454,368 A * | 10/1995 | Tarulli | 128/205.26 |
| 5,853,361 A | 12/1998 | Kobayashi et al. | |
| 5,908,776 A * | 6/1999 | Burbaum et al. | 435/288.3 |
| 6,001,057 A * | 12/1999 | Bongiovanni et al. | 600/21 |
| 6,036,633 A * | 3/2000 | Hodge | 600/22 |
| 6,074,340 A * | 6/2000 | Sweeney et al. | 600/22 |
| 6,117,687 A * | 9/2000 | Hugh | 436/183 |
| 6,641,521 B1 * | 11/2003 | Kolarovic | 600/22 |

* cited by examiner

PROCESS FOR HUMIDIFYING THE USEFUL SPACE IN AN INCUBATOR AND IN A CONTROLLED ATMOSPHERE INCUBATOR

BACKGROUND OF THE INVENTION

1. Field of the Invention

The invention pertains to a method to humidify a work space in a gas-fed incubator, wherein water is evaporated in a heatable pan in the floor area of an inner container surrounding the work space until a predetermined temperature is reached. The invention also pertains to a gas-fed incubator.

Here, the invention involves a method according to the basic principle of passive humidification, wherein at the same time as the temperature-controlled heating of the inner container, the atmosphere of the inner container is humidified by evaporation of water from a heatable pan until a predetermined temperature is reached and the relative humidity is maintained in a state of equilibrium (dynamic equilibrium of condensation and evaporation).

2. Description of the Related Art

A gas-fed incubator for cultivating human or animal cells or tissues is known from DE 3815528 C1. This incubator has an inner housing that can be closed by means of a door. Further, the incubator is surrounded by a heat-insulating outer housing, wherein a humidifier is arranged in the floor area of the inner housing. Electrical heating elements are arranged underneath the floor of the inner housing and in the area of the side walls. The humidifier is realized in the form of a floor pan holding a water bath, wherein the heating elements lie flat against the outside of the floor. The heating elements are bent upwards in the area of the side walls and the rear wall of the inner housing such that they project past the plane of the inner-housing floor and thus heat the transition region between the floor and side or rear wall. In order to achieve a high relative humidity in the test space, the water is heated quickly and uniformly, wherein condensation on the inner wall is prevented to a large degree.

Further, an incubator with controlled interior atmosphere is known from U.S. Pat. No. 6,117,687 A, in which a chamber used as the interior is surrounded by a heated jacket filled with water. A glass door sealing the interior has an electrically conductive coating for heating. Furthermore, disturbances in the environment of the incubator during operation are compensated for by the regulator. This involves a relatively complicated design.

SUMMARY OF THE INVENTION

The present invention was devised to eliminate the above described disadvantages. One object of the invention is to shorten the humidity recovery time in the atmosphere of the inner container containing the work space with relatively simple means if the inner container is opened or the environmental conditions change drastically.

The object is realized for the method by means of detecting, after a door to the inner container is opened, the open time U0 until it is closed and setting a period U1 during which the pan is heated depending on the open time of the inner container.

One advantage is that a humidification regulator can be eliminated. Additional advantages of the method can be seen in that the incubator is in the position:

1. to react to different ambient temperatures without exceeding a value of 96% for the relative humidity, which could lead to condensation in the device with the corresponding risk of contamination,
2. to react to different time sequences of temperature and relative humidity for different loads so that neither a predetermined temperature value or the relative humidity of 96% is exceeded,
3. to guarantee improved humidity recovery times even for multiple door openings, while for purely passive humidification systems, the humidity recovery time degrades with each additional door opening and it can take a very long time until the device contains an equalized interior atmosphere.

In a preferred configuration of the method, the period U1 has, on the one hand, only a heating phase with the running time T2 if the open time U0 is within a predetermined time interval T1, and on the other hand, the period U1 also contains a secondary heating phase with the running time T3 if during the heating phase with the running time T2 at an intensity that is dependent on the time interval between the two last openings of the inner container.

The task is solved for the device for a gas-fed incubator with a work space in a temperature-controlled inner container that can be closed by means of a door, which is surrounded by a heat-insulating outer housing with an external door, and which has, in the floor area of the inner container, a humidifier with at least one controllable heating element for the atmosphere of the inner container in the form of a pan holding a water bath, such that the door for closing the inner container has a door switch that is electrically connected to the input of a control device which controls the power supply for one or more heating elements.

Advantageously, one or more heating elements are arranged in the region of the floor area outside of the inner container.

In a preferred configuration of the incubator according to the invention, outside of the heating element or heating elements in the plane of the floor area, there are additional heating elements in the area of the side walls and the rear wall of the inner container such that they project past the plane of the inner container floor. All of the heating elements are located outside of the inner container.

In addition, it is possible to realize the door that seals the inner container as a heatable glass door so that under unfavorable conditions, condensation on the glass pane can be prevented.

The heating elements of the two side walls or the rear wall and also, if necessary, of the heatable glass door, are referred to as a wall heater in the following for the sake of simplicity.

In a preferred embodiment, the control device has at least one time element, which helps to evaluate the time function for opening and closing of the door switch.

It is an advantage for the growth chamber or incubator to be in a position to react to door openings of different lengths of time, as well as to different time intervals between the door openings and to control the supplied amount of heat correspondingly.

Furthermore, the door switch is advantageously associated with an inner door that seals tight the inner container.

In an advantageous configuration of the gas-fed incubator, the one or more heating elements of the humidifier can be controlled by means of the control unit such that they can also be used as part of the control loop for the temperature control in the inner container. The ability to switch the elements in and out has proven to be particularly advantageous for savings relative to the number of heating elements. In addition, there are heating elements in the area or in the surroundings (rear wall, side walls) of the inner container, which are always used as control elements in the control loop for the temperature control. The heatable glass door can also be connected to the temperature control.

Preferably, both the function of the control device and also the function of a regulator are programmed in a digital computer, which gives a cost-effective design.

The temperature difference between the desired value and the actual value is dependent on the device specifications 230/120 V and stainless steel/copper inner container.

The advantages and features of the present invention will become more apparent from the following detailed description of the preferred embodiments of the present invention when viewed in conjunction with the accompanying drawings.

DETAILED DESCRIPTION OF THE PREFERRED EMBODIMENTS

Figure 1A:
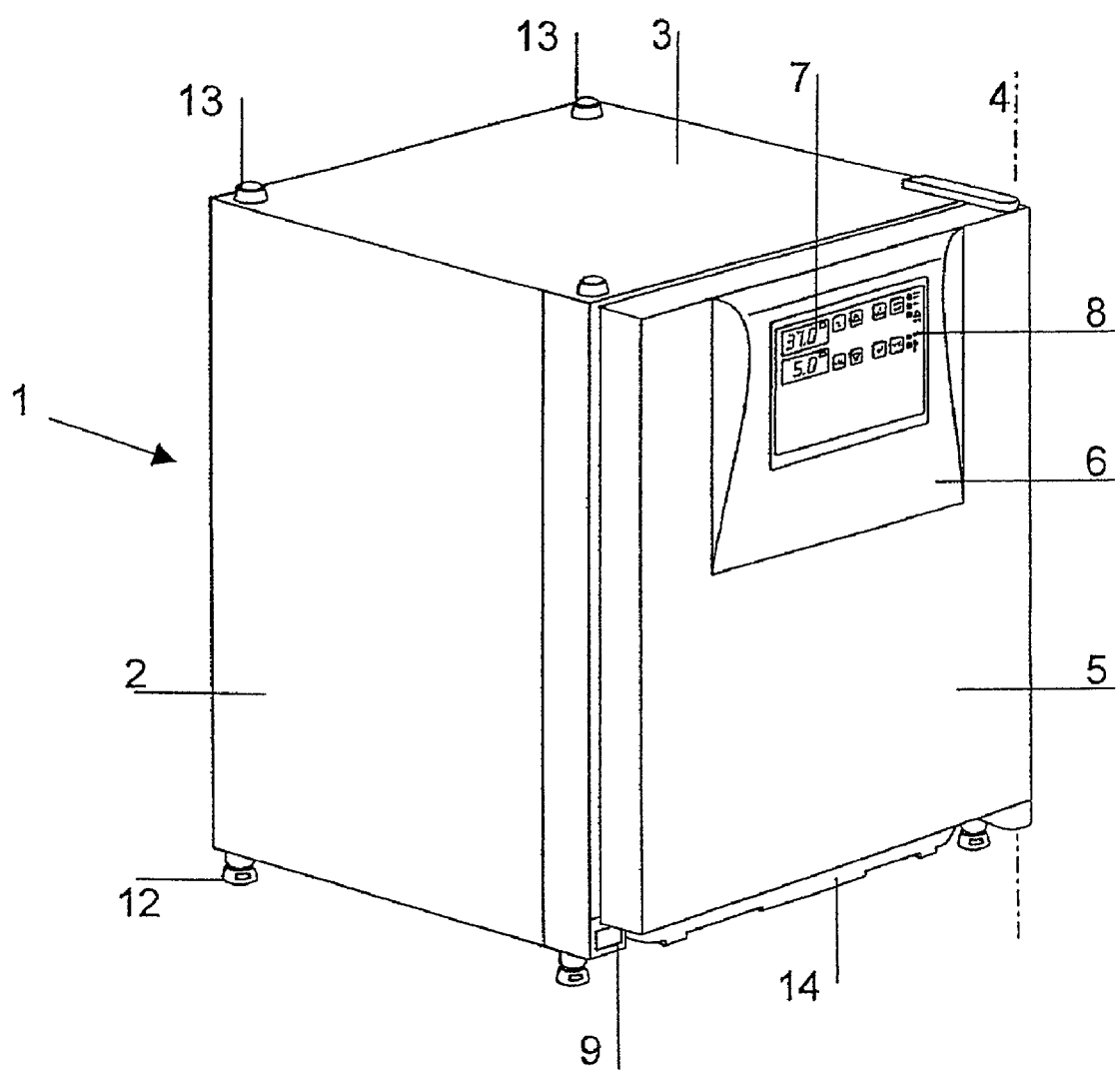
FIG. 1a shows a closed gas-fed incubator in a three-dimensional view.

According to FIG. 1a, the incubator has a housing 1 that can be sealed from the outside and that has side walls 2, a rear wall that is not visible, and also floor and cover plate 3, wherein a front door 5 that can pivot about a vertical axis 4 seals the housing 1 against the surrounding atmosphere. The front door has a control panel 6 with display elements 7 and also activation elements 8, wherein the actual operating switch 9 is arranged in the lower left region of a frame plate 11 surrounding the front opening. This region is not covered by the closed front door 5. The bottom side of housing 1 of the incubator has feet 12 that can be adjusted in height and that are realized such that they can be fixed to stacked elements 13 of the cover plate of an incubator housing that is already present, if necessary. In this way, it is possible to stack two or three incubators one on another. Furthermore, in the lower part of the front region of the housing 1, there is a small hole 14 for temporary preserving of samples for the incubator.

Figure 1B:
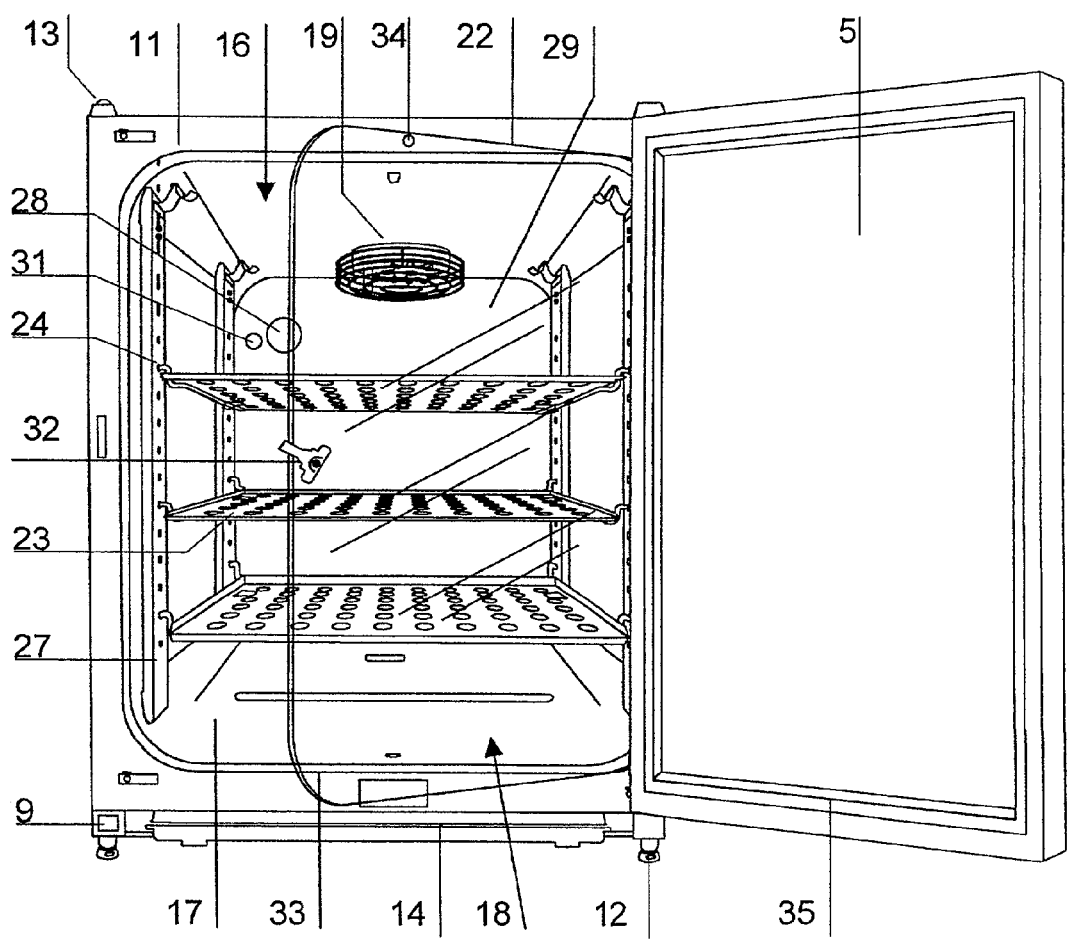
FIG. 1b shows, in a perspective view, a gas-fed incubator with a floor pan holding a water bath in the inner container, as is essentially already known from DE 3815528 C1 or the corresponding EP 0340341 B1.

According to FIG. 1b, the outer housing 1 of the incubator has a heat-insulating body that is not visible here and that surrounds an inner container 16 which contains in its floor area 17 a pan 18 holding a water bath. For humidifying the atmosphere in the inner container 16, the pan 18 is heated by heating elements in the floor area or in the lower region of the rear wall and side walls, so that a high relative humidity can be generated relatively quickly in the atmosphere of the inner container 16. However, the heating elements are advantageously arranged in the surroundings of the floor area outside of the inner container 16. Thus, the heating elements are located between the inner container and the outer housing 1 so that the interior of the inner container has no heating elements at all and hence can be advantageously cleaned by simple means in a simple way.

For controlling the atmosphere of the interior of the inner container 16, there is a control system, which has a sensor for detecting the interior temperature and a $CO_2$ sensor for detecting the $CO_2$ content in the atmosphere each with a separate control loop. For holding the two sensors, there is a measurement cell 19 that is located in the cover region of the inner container 16, wherein the measurement cell has a fan so that each sensor (temperature and $CO_2$ content sensor) can be supplied quickly with up-to-date measurement values.

The measurement values detected by the sensors are converted into electrical signals and then compared as actual value signals with previously set desired value signals. For a deviation (difference between desired value and actual value), a control signal is output to adjust the temperature by means of heat supply by the heating elements or to adjust the $CO_2$ content by means of gas supply into the interior of the inner container.

The control of the $CO_2$ content in the inner container is done according to a method like those known, e.g., from DE-PS 196 57 520, DE-PS 29 24 446, or DE 33 15 085 C2.

The inner container 16 is accessible through an inner door 22 which is preferably configured as a (heatable) glass door for the purpose of optical control of the cultivation of the goods located in the interior. Furthermore, according to FIG. 1a the outer housing 1 can be closed with the outer door 5, wherein the inner and outer doors are each arranged in the front region of the incubator.

Furthermore, as an example of inner equipment in the inner container 16, horizontal insertion sheets 23 that are used for holding goods for treatment can be seen in FIG. 1b. The insertion sheets 23 rest on support clamps 24 that are fixed in openings 26 of vertical carrier sections 27 in the side wall region.

In the region of the rear wall 29 of inner container 16, there is a pipe duct 28 can be seen with a gas outlet directed inwards for the $CO_2$ supply into the interior of the inner container.

Furthermore, in the region of rear wall 29, a pressure-equalization opening 31 can be seen in order to exhaust displaced air during gas inlet.

The inner door 22 formed as a glass door is to be fixed by means of a lockable handle 32, wherein a subsequent closing of the outer door is only possible for proper locking of the inner door. For sealing the inner container 16, there is an elastic seal 33 surrounding the front opening on the frame plate 11, and the inner door 22 is pressed against this seal. Furthermore, for closing the inner door 22, a door switch 34 also located in the frame plate 11 is activated so that by means of controlling the heating elements arranged in the floor area, a quick recovery of the desired atmosphere in the inner container is possible.

It can be further seen from FIG. 1b that the inward facing side of the outer door 5 has a surrounding seal 35 that is pressed against the frame plate 11 when the outer door 5 is closed.

With the aid of FIG. 2, a disturbance of the interior atmosphere due to the inner container 16 being opened is described in the following.

For opening of the inner door 22, the air humidity in the inner container 16 falls greatly, so that the atmosphere required for the cultivation of the object to be treated in the interior space must be recovered quickly. Here, according to the process flow diagram in FIG. 2, at first the open time U0 of the inner door for the inner container is measured and compared with a predetermined time interval T1. If the open time U0 is within the predetermined time interval T1, the pan 18 filled with water is heated at the intensity of a set value S independent of the control loop for a predetermined period T2 by means of one heating element or heating elements, wherein the set value S is dependent on a predetermined period U3 between the last two door openings. In practice, a set value S is used that is preferably proportional to the period U3. If the condition U0<T1 is true, then at the end of the period T2 the heating with set value S is ended and a heating of the interior of inner container 16 is performed based on the typical temperature control.

If the open time U0 of door 22 for the inner container 16 exceeds the predetermined time interval T1, then in addition to phase T2, there is a secondary phase T3 after the period T2, wherein a set value S1 independent of the control loop likewise controls the intensity of heating. The heating with set value S1 is ended as soon as a predetermined temperature is reached in the inner container. However, the controlled heating with S1 ends at the latest with the completion of the running time for phase T3 independent of the temperature produced in the inner container 16.

The secondary phase T3 can be eliminated as long as the deviation (difference between desired value and actual value of the temperature in the inner container) is within a predetermined range. In practice, this range is between 0.6° C. and 1.4° C. according to the particular device specifications.

Figure 3:
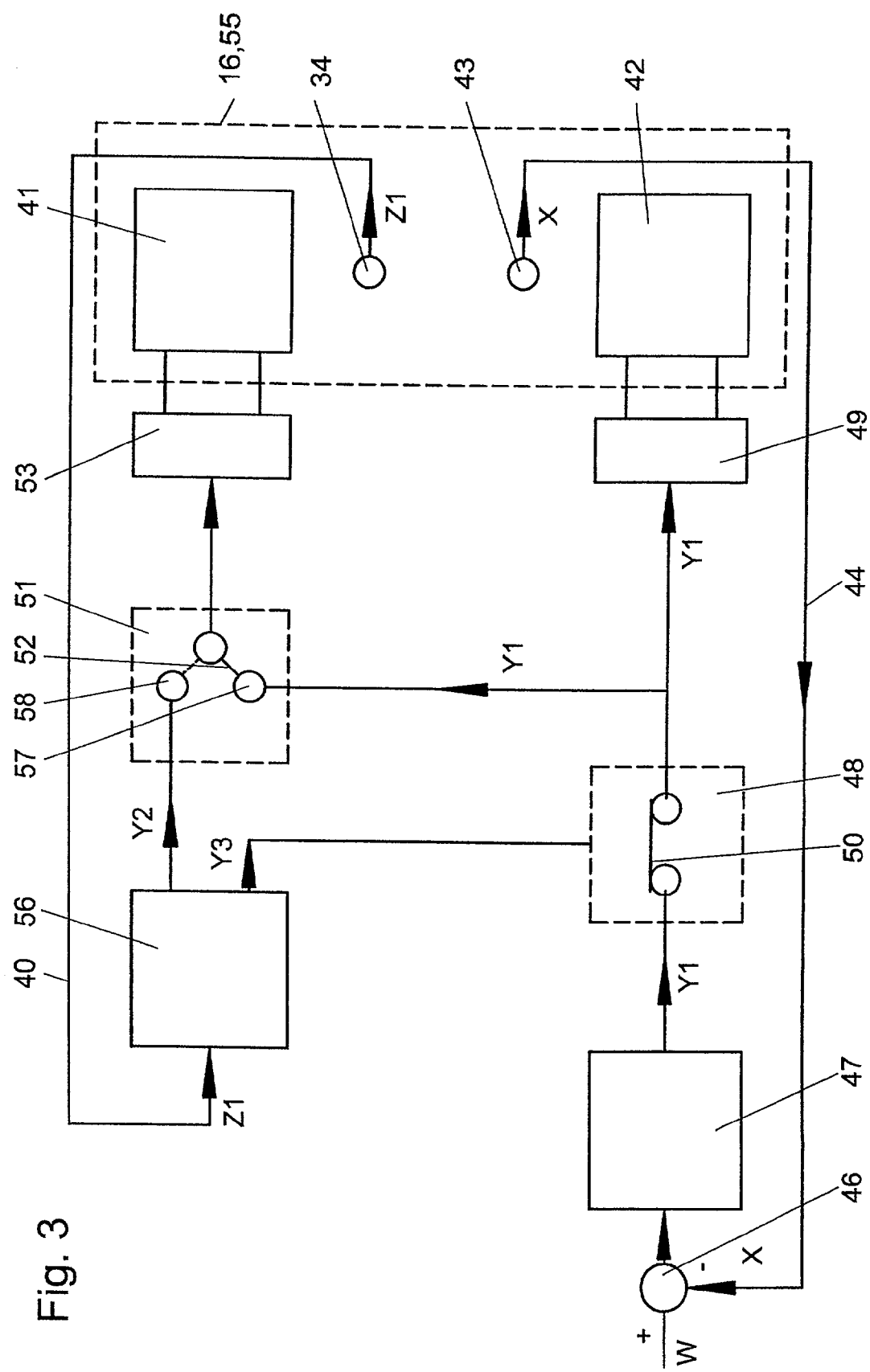
FIG. 3 shows functional units of the incubator according to the invention for performing the method in a block diagram, and these functional units are shown as discrete components for easier understanding, even when in practice they are realized through programs and databases for a digital computer.

With reference to FIG. 3, the functional connection of the method is explained in more detail by a block diagram, wherein the individual components or their functions are represented symbolically by blocks and their connections are represented schematically. In practice, however, the functions of regulator, control device, and switch or interrupter are performed by a programmable digital computer, so that virtually no individual components are used.

From FIG. 3, the inner container 16 contains a floor heater 41, a wall heater 42 (including heating elements for rear wall, left and right side walls and if necessary, heatable glass door for closing the inner container), and also a temperature sensor 43 (as part of measurement cell 19 according to FIG. 1b), wherein these components are formed as part of a control loop for temperature control in the inner container. Here, after measurement of the temperature in the inner container by temperature sensor 43, an actual value signal X corresponding to the measurement value is guided over line 44 to the inverting input of regulator input 46, while the previously set desired value W is applied to the non-inverting input (regulator input 46). The associated regulator is designated by reference numeral 47. A possible deviation of the actual value signal X from the predetermined desired signal W is then supplied as a difference value (W−X) to the regulator 47, which outputs a set signal Y1 based on its control characteristics (e.g., PID regulator with previously set parameters). The set signal Y1 is further guided over an optional interrupter switch 48 to a control element 49 which activates the wall heater 42. Parallel with this process, in the stable control operation (without external disturbances) the set signal Y1 is further guided over a controllable switch 51 with contact mechanism 57 containing a switching contact 52 to a control element 53 for the control of the floor heater 41. The control elements 49, 53 provide for the supply of electrical energy to each connected heater 42, 41, wherein these components together with temperature sensor 43 form a control path in the sense of a control process for a closed inner container 16. This control path is included in the schematically represented block 55 illustrated symbolically in FIG. 3. This block also corresponds to the interior of the schematically represented inner container 16. If the actual temperature value signal X from the control path now deviates from desired value W in stable operation, such a deviation (W−X) leads to a set signal Y1 output at the output of regulator 47 corresponding to the set values S or S1 according to the flow diagram in FIG. 2, wherein the set signal Y1 activates the power supply of each heater 42 and 41 by means of the corresponding control elements 49 and 53 until the measurement value (actual value X) detected by temperature sensor 43 corresponds to the desired temperature value W or the deviation is within a predetermined tolerance range.

Figure 2:
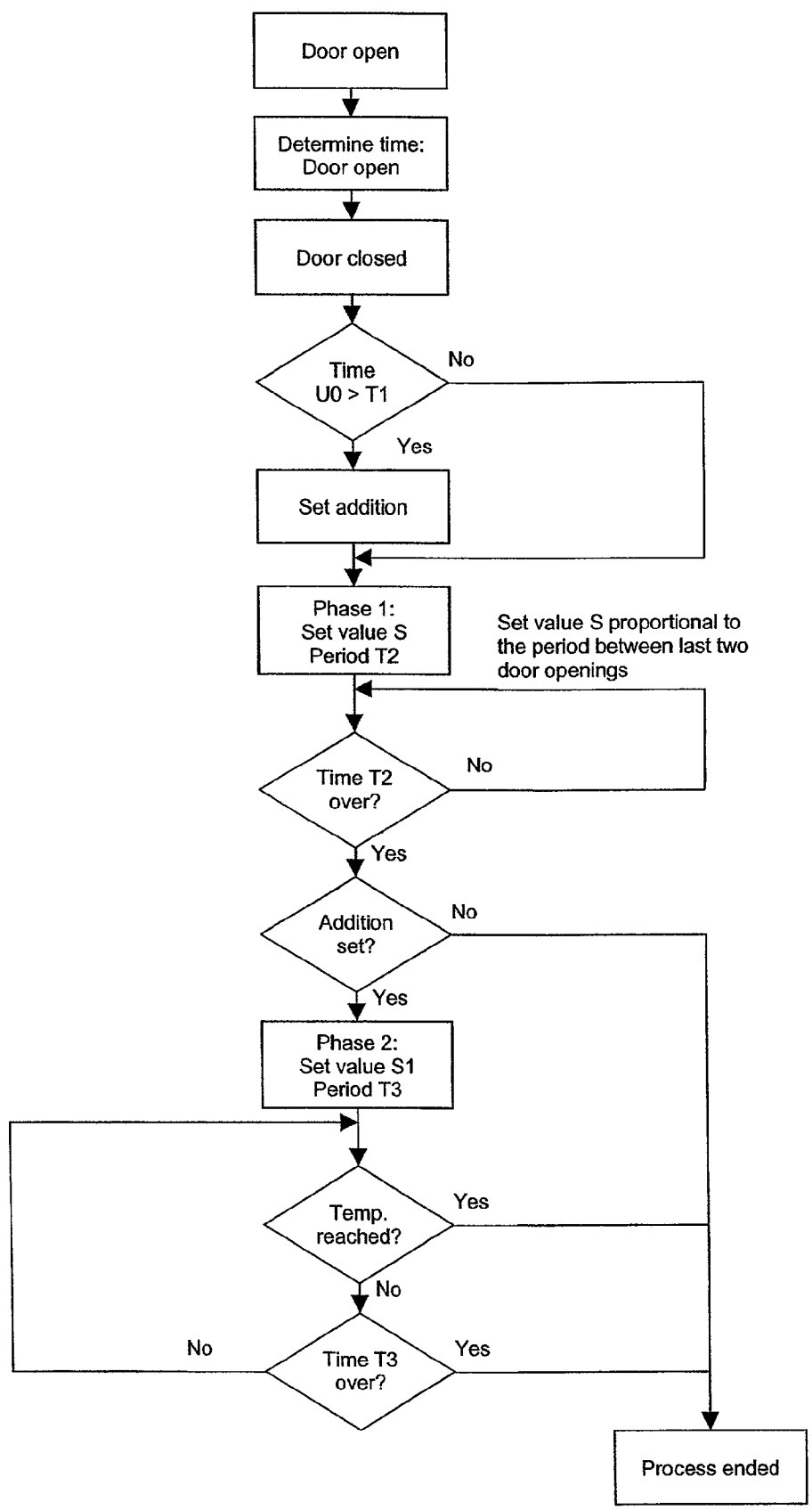
FIG. 2 shows the functionality of the method according to the invention schematically in a process flow diagram.

For example, if the inner container 16 according to FIG. 1 is opened by means of the inner door 22, a disturbance signal Z1 is sent from the door switch 34 illustrated symbolically in FIG. 3 over line 40 to a series-connected control device 56 with installed time element and comparator, wherein the disturbance signal Z1 contains information about open time U0 and the number of opening processes of the inner container 16 according to the flow diagram in FIG. 2.

Additional disturbances, e.g., the ambient temperature of the incubator or the starting temperature of the objects to be treated, which are designated with Z2, Z3, can be included in the control loop; however, for the purpose of an easier overall view, they are not shown in FIG. 3.

If the humidity in the inner container 16 now decreases greatly due to opening of the door 22, a set signal Y2 is output from the control device 56 to the input of the switch 51 based on the disturbance signal Z1. The moving switch contact 52 is then switched from the contact position 57 for the stable control operation to contact position 58, so that the control element 53 can be controlled by means of signal Y2 for the power supply to the connected floor heater 41 directly from the control device 56. According to FIG. 2, the control element is controlled with a relatively strong signal S as set signal Y2, whereby a strong heating of the pan 18 containing water (FIG. 1b) in the floor area of the inner container 16 is performed to increase the humidity. If necessary, a secondary phase with set value S1 as set signal Y2 follows if the condition for the setting of a secondary run according to FIG. 2 is fulfilled.

As soon as the secondary phase according to the flow diagram in FIG. 2 ends, switch contact 52 is switched back to its original position at position 57, so that now set signal Y1 from regulator 47 is applied to control element 53 for routine control of the floor heater 41.

In an optional embodiment of control device 56, a signal from door switch 34 due to the inner door or glass door being opened is used to control the aforementioned interrupter switch 48 as an additional set signal Y3, so that by opening a switch contact 50, the set signal Y1 is interrupted by regulator 47. This means that the control elements 49 and 53 can no longer be controlled. However, this optional door opening signal is only effective during the actual door open time, so that after the door of the inner container is closed, set signal Y1, in turn, is applied at least to control element 49 and thus condensation from the humidity on the inner wall of the inner container is prevented by operation of the wall heater 42. As soon as the secondary phases according to flow diagram in FIG. 2 are completed, the control loop returns to its original operating state, wherein only the set signal Y1 that is characteristic for the stable operation is still supplied to the control elements 49 and 53 for the wall heater 42 and the floor heater 41.

In one embodiment of the incubator, in which the door 22 closing the inner container 16 is replaced by a gas barrier, a door switch responding to the outer door gives its signal to control device 56, wherein the other sequence corresponds to the method from FIG. 2.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

We claim:

1. A gas-fed incubator with a work space comprising:
   an inner container
   a heat-insulating outer housing that surrounds the inner container;
   a humidifier with at least one controllable heating element for an atmosphere of the inner container in the form of a pan holding a water bath, positioned in the floor area of the inner container; and
   a door with temperature control that is configured to close the inner container;
   a door switch positioned with the gas fed incubator such that it detects the opening of the door,
   a control device electrically connected to the door switch, wherein the control device is configured to control a power supply for the at least one controllable heating element, the control device is configured to increase a duration of heat radiating from the controllable heating element based on a time period that the door is open and a time period between at least the last two door openings, to rapidly increase the humidity.

2. The gas-fed incubator according to claim 1, wherein the at least one heating element is arranged in a region of the floor area outside of an interior of the inner container.

3. The gas-fed incubator according to claim 1, wherein the control device has at least one time element adapted to evaluate the time function of the door switch.

4. The gas-fed incubator according to claim 2, wherein the control device has at least one time element adapted to evaluate the time function of the door switch.

5. The gas-fed incubator according to claim 1, wherein there is an outer door for closing the outer housing and an inner door that tightly seals the inner container, and wherein the door switch is associated with the inner door.

6. The gas-fed incubator according to claim 2, wherein there is an outer door for closing the outer housing and an inner door that tightly seals the inner container, and wherein the door switch is associated with the inner door.

7. The gas-fed incubator according to claim 3, wherein there is an outer door for closing the outer housing and an inner door that tightly seals the inner container, and wherein the door switch is associated with the inner door.

8. The gas-fed incubator according to claim 4, wherein there is an outer door for closing the outer housing and an inner door that tightly seals the inner container, and wherein the door switch is associated with the inner door.

9. The gas-fed incubator according to claim 1, wherein the power supply for the at least one heating element of the humidifier can be controlled by means of the control device such that the at least one heating element can also be used for temperature control in the inner container.

10. The gas-fed incubator according to claim 2, wherein the power supply for the at least one heating element of the humidifier can be controlled by means of the control device such that the at least one heating element can also be used for temperature control in the inner container.

11. The gas-fed incubator according to claim 3, wherein the power supply for the at least one heating element of the humidifier can be controlled by means of the control device such that the at least one heating element can also be used for temperature control in the inner container.

12. The gas-fed incubator according to claim 5, wherein the power supply for the at least one heating element of the humidifier can be controlled by means of the control device such that the at least one heating element can also be used for temperature control in the inner container.

13. The gas-fed incubator according to claim 1, also comprising at least one additional heating element which is provided in a region of at least one of a side wall and a rear wall of the inner container for temperature control of the inner container.

14. The gas-fed incubator according to claim 2, also comprising at least one additional heating element which is provided in a region of at least one of a side wall and a rear wall of the inner container for temperature control of the inner container.

15. The gas-fed incubator according to claim 3, also comprising at least one additional heating element which is provided in a region of at least one of a side wall and a rear wall of the inner container for temperature control of the inner container.

16. The gas-fed incubator according to claim 5, also comprising at least one additional heating element which is provided in a region of at least one of a side wall and a rear wall of the inner container for temperature control of the inner container.

17. The gas-fed incubator according to claim 9, also comprising at least one additional heating element which is provided in a region of at least one of a side wall and a rear wall of the inner container for temperature control of the inner container.

18. The gas-fed incubator according to claim 1, comprising a digital computer wherein a function of the control device and a function of a regulator for control of an interior atmosphere of the inner container are programmed.

19. The gas-fed incubator according to claim 2, comprising a digital computer wherein a function of the control device and a function of a regulator for control of an interior atmosphere of the inner container are programmed.

20. The gas-fed incubator according to claim 3, comprising a digital computer wherein a function of the control device and a function of a regulator for control of an interior atmosphere of the inner container are programmed.

21. The gas-fed incubator according to claim 5, comprising a digital computer wherein a function of the control device and a function of a regulator for control of an interior atmosphere of the inner container are programmed.

22. The gas-fed incubator according to claim 9, comprising a digital computer wherein a function of the control device and a function of a regulator for control of an interior atmosphere of the inner container are programmed.

23. The gas-fed incubator according to claim 13, comprising a digital computer wherein a function of the control device and a function of a regulator for control of an interior atmosphere of the inner container are programmed.

24. The gas-fed incubator according to claim 1, wherein the inner door is a heatable glass door.

25. The gas-fed incubator according to claim 2, wherein the inner door is a heatable glass door.

26. The gas-fed incubator according to claim 3, wherein the inner door is a heatable glass door.

27. The gas-fed incubator according to claim 5, wherein the inner door is a heatable glass door.

28. The gas-fed incubator according to claim 9, wherein the inner door is a heatable glass door.

29. The gas-fed incubator according to claim 13, wherein the inner door is a heatable glass door.

30. The gas-fed incubator according to claim 18, wherein the inner door is a heatable glass door.

* * * * *